United States Patent [19]

Farin

[11] 4,244,371

[45] Jan. 13, 1981

[54] HIGH-FREQUENCY SURGICAL APPARATUS

[75] Inventor: Günter Farin, Tübingen-Hirshau, Fed. Rep. of Germany

[73] Assignee: Erbe Elektromedizin GmbH & Co. KG, Tübingen, Fed. Rep. of Germany

[21] Appl. No.: 22,376

[22] Filed: Mar. 20, 1979

Related U.S. Application Data

[63] Continuation-in-part of Ser. No. 841,983, Oct. 13, 1977, Pat. No. 4,171,700.

[30] Foreign Application Priority Data

Oct. 13, 1976 [DE] Fed. Rep. of Germany ....... 2646229

[51] Int. Cl.$^3$ .................................................. A61B 17/39
[52] U.S. Cl. ............................ 128/303.14; 128/303.17
[58] Field of Search ...................... 128/303.13, 303.14, 128/303.15, 303.17, 303.18

[56] References Cited

U.S. PATENT DOCUMENTS

| | | | |
|---|---|---|---|
| 3,478,744 | 11/1969 | Leiter | 128/303.17 X |
| 3,683,923 | 8/1972 | Anderson | 128/303.14 |
| 4,051,855 | 10/1977 | Schneiderman | 128/303.14 |

FOREIGN PATENT DOCUMENTS

| | | | |
|---|---|---|---|
| 2044078 | 5/1972 | Fed. Rep. of Germany | 128/303.14 |
| 2150586 | 4/1973 | France | 128/303.14 |

*Primary Examiner*—Lee S. Cohen
*Attorney, Agent, or Firm*—Frishauf, Holtz, Goodman & Woodward

[57] ABSTRACT

In a high-frequency surgical apparatus having a number of electrode-connections for a neutral electrode and a number of electrodes, respectively, for monopolar and bipolar operation, a single high-frequency generator operating through a transformer with monopolar and bipolar secondaries designed to work into different impedance loads is provided in combination with a multipole switch for switching over between bipolar and monopolar use. A warning signal is produced only if the switch is set for a monopolar use, even if the neutral electrode is not properly connected. The bipolar output may be used independently of whether a neutral electrode is connected to the apparatus or not. In this manner unintended injuries or damage by a contact with an electrode are avoided. Examples for the field of use of such electrosurgery units are Dermatology, Gynaecology, Ophthalmology, Dental Surgery, ENT and Cosmetic Surgery.

4 Claims, 1 Drawing Figure

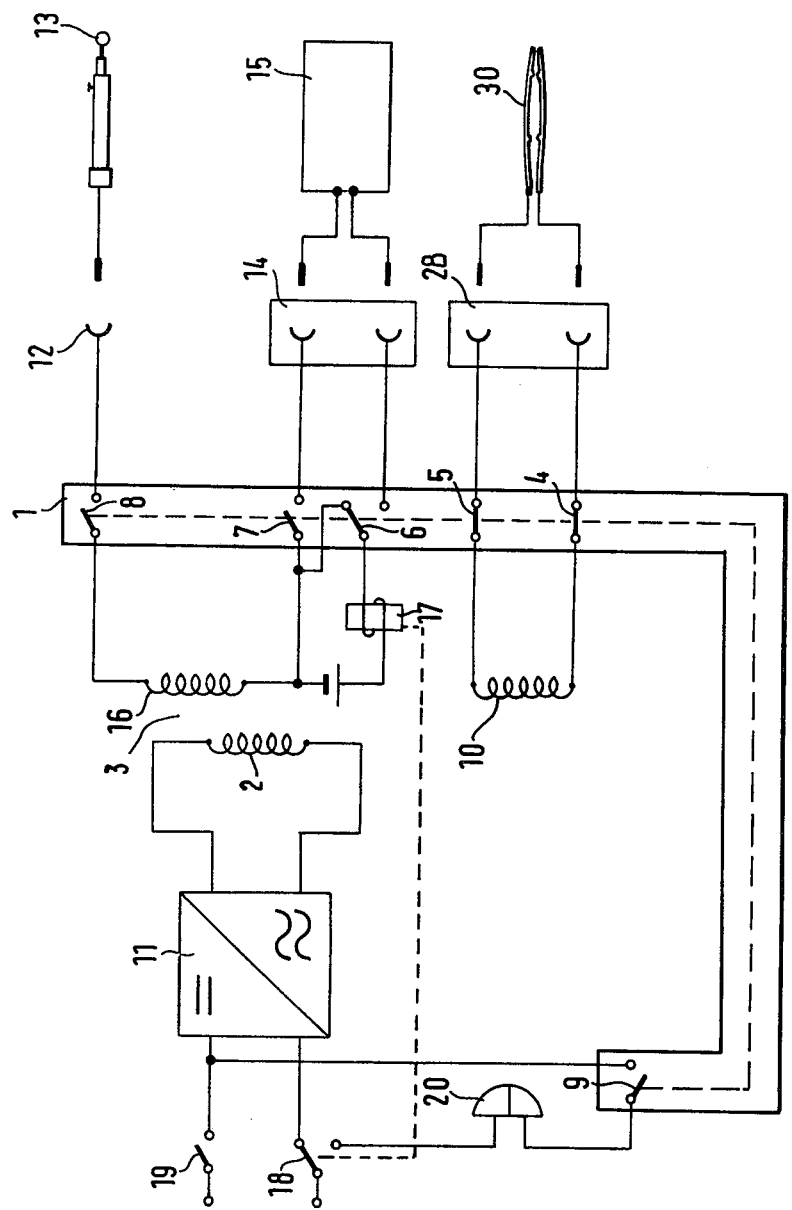

HIGH-FREQUENCY SURGICAL APPARATUS

This application is a continuation-in-part of my copending application, Ser. No. 841,983, filed Oct. 13, 1977, now U.S. Pat. No. 4,171,700, the disclosure of which is incorporated herein by reference.

The present invention relates to a high-frequency surgical apparatus, e.g., for use in producing coagulation of body tissues in high-frequency electro-surgery. Such surgical apparatus is normally provided with a neutral electrode and activatable electrodes for monopolar and bipolar operation, and is provided with a protective circuit, which in the case of an interruption of the electrical circuit between the neutral electrode and its connections at the apparatus also interrupts the supply of energy from the high-frequency generator to the active electrode or electrodes and indicates the interruption by an alarm signal.

In the case of known high-frequency surgical apparatus of this type, which are provided with electrode contacts for a monopolar as well as for a bipolar use, the high-frequency current for the monopolar as well as for the bipolar use is supplied from a single high-frequency generator. Though it is possible in the case of such known surgical apparatus to adjust the output power for the monopolar use and the bipolar use, respectively, independently from each other at the apparatus, still a number of problems are involved in the practical use of such surgical apparatus.

During the activation of the high-frequency generator, high-frequency electrical voltage is present simultaneously on all connections, this voltage being applied to the connections of both the monopolar and the bipolar electrodes.

If monopolar and bipolar electrodes are simultaneously connected with the surgical apparatus, the danger exists, that the excited but unused electrode may cause damage to materials and devices or even injure the patient or attending personnel. In the case of a monopolar use of such surgical apparatus with higher output power, it is necessary, furthermore, to provide a protective circuit, which in the case of a break of the electrically conducting connections between the neutral electrode and its contact at the apparatus also interrupts the supply of energy to the active electrode and indicates the interruption by an alarm signal. Therefore, it is also necessary in the case of a bipolar use, in which a neutral electrode is not needed, to connect a neutral electrode, since otherwise the protective circuit of the neutral electrode, which is provided for safety reasons, would hinder the activation of the high-frequency generator. Furthermore, there is risk of injury especially in the case of high-frequency surgical apparatus in which the neutral electrode has a "floating" output (i.e., where the neutral electrode and therewith also the patient connected to the neutral electrode are at a high-frequency potential relative to ground potential). This voltage has its maximum value if the active output of the monopolar circuit is short-circuited to the ground potential. Accidental injury is possible if the active electrodes are brought in contact with a grounded object unintentionally. In such apparatus, the danger always exists that high-frequency current will flow from the neutral electrode into the bipolar electrode and return through practically unavoidable leakage capacitance to the high-frequency generator. Such currents should be avoided in the bipolar mode of operation.

It is, therefore, the primary object of the present invention to provide a high-frequency surgical apparatus which avoids problems of the above-mentioned type, so that on the one hand the operating reliability (safety) can be improved and on the other hand the control, operation and use of the apparatus is simplified.

In my copending application, Ser. No. 841,983, now U.S. Pat. No. 4,171,700, apparatus comprising two separate high-frequency generators, respectively, for monopolar and bipolar surgical apparatus was disclosed. It is an object of the present invention to obtain similar safety of operation with a single high-frequency generator.

SUMMARY OF THE INVENTION

Briefly, a single high-frequency generator is arranged to provide its output through two transformer secondary windings not connected to (electrically isolated from) each other but energized from the same source, preferably a common primary winding, and a switch-over means for switching over between bipolar and monopolar use is provided, so that in the case of the bipolar use the protective circuit to assure connection of the neutral electrode is switched off. The respective secondary windings are designed to work into different load impedances usually about 500 ohms for monopolar operation and about 100 ohms for bipolar operation.

Preferably the switch-over means contains switches coupled with each other and connected in such a manner between the output of the high-frequency generator and the electrode connections, that in one switch position only the electrode connections for bipolar electrodes are connected with the high-frequency generator and one of the switch elements then disconnects the protective circuit. In the other switching position only the electrode connections for the neutral electrode and the electrode connection for the monopolar electrode are connected, and the mentioned switch element connects the alarm device with the protective circuit. Therefore, in the case of bipolar use the high-frequency generator will be activated even if the neutral electrode is not connected to the high-frequency surgical apparatus, whilst in the case of monopolar use the activation of the high-frequency generator is only possible if the neutral electrode is properly connected with the high-frequency surgical apparatus.

The invention is further described by way of specific examples with reference to the annexed drawings, in which the single FIGURE is a circuit diagram of an embodiment of a high-frequency surgical apparatus in accordance with the invention, containing a single high-frequency generator and a switch-over means.

The drawing shows the high-frequency generator 11, connected to a source of power through switches 18 and 19 which are independently operated. The switch 19 represents a foot switch for controlling the periods of operation of the high-frequency generator 11, as is convenient for a surgeon whose hands may be busy using a connected electrode or other surgical apparatus. The switch 18 is controlled by a relay 17 as further described below and, of course, both the switches 18 and 19 must connect the high-frequency generator 11 with the source of power not shown in the diagram in order for the generator to operate. The output of the high-frequency generator 11 is connected to the primary coil 2 of the transformer 3, which has a first secondary coil 16 and a second secondary coil 10.

In the illustrated embodiment of the invention, the switch-over means for selection of bipolar or monopolar output comprises switches 4 to 9 coupled with each other. In the shown switching position only the electrode-connections 28 for a bipolar electrode 30 are connected to the high-frequency generator 11 through the second secondary coil 10. In the other position of the switches, the electrode connections 14 for a neutral electrode 15 and an electrode-connection 12 for a monopolar electrode 13 are connected through the first secondary coil 16 of the high-frequency generator 11. A relay coil 17 is provided in the protective circuit, which in the case of an interruption of the electrically conducting connection between the neutral electrode and its connection at the apparatus moves the switch 18 (its contacts) to the lower position and interrupts the energy supply to the active monopolar electrode 13 and actuates an alarm device 20. When the circuit is, as shown, switched over for bipolar operation, the relay coil 17 is kept energized. The protective circuit is thereby disabled and operability of the h-f generator is assured.

Operation will now be reviewed in more detail. In the position of the switches 4 to 9 as shown in the drawing, bipolar operation takes place, while the electrode-connections 12 for the monopolar electrode 13 and the electrode connections 14 for the neutral electrode 15 are separated from the secondary circuit 16 of the high-frequency generator 11. Since the switch 6 closes the energizing circuit for the relay 17, in the shown position of the switch 18, the current supply for the high-frequency generator 11 is prepared. If then a finger- or foot-switch 19 is closed, the high-frequency generator 11 is switched on and high-frequency current may be drawn from the electrode-connections 28, while no voltage is supplied to the electrode-connections 12 and 14. Regardless of whether the neutral electrode 15 is connected with the electrode-connections 14 or not, the alarm device 20 is then unable to produce an alarm signal.

If the switching-over means 1 is switched over to monopolar use, the switches 6 and 7 connect the neutral electrode 15 through the electrode-connections 14. If the neutral electrode 15 is connected with the electrode-connections 14, the energizing circuit for the relay 17 is closed and the switch 18 in the shown position readies the current supply to the high-frequency generator 11. Upon closing of the finger- or foot-switch 19 the high-frequency generator 11 may then be switched on. The electrode-connections 12 and 14 are then supplied with the high-frequency current through the switches 8 and 7 from the secondary coil 16 of the high-frequency generator, while the electrode-connections 28 are not under voltage, since the switches 4 and 5 are opened. Upon separating the neutral electrode 15 in the position of the switches for monopolar use from the electrode-connections 14, the operating circuit for the relay 17 is interrupted and the switch 18 deenergizes the high-frequency generator 11, and the operating circuit of the alarm device 20 is closed by the switches 18 and 9 to produce an alarm signal.

There is no electrical connection (there is electrical isolation) between the respective circuits of the secondary coils 10 and 16. Furthermore, although this is not indicated by the representations of these coils in the drawing, the coil 16 has more turns than the coil 10, because it is designed to couple the generator 11 to a load impedance of several hundred ohms, usually about 500 ohms, and generally between 300 and 600 ohms while the coil 10 is designed to couple the same generator 11 to a load impedance of about 100 ohms and generally between 50 and 200 ohms. These different impedance levels have been found typical of practice in blood coagulation work, for instance, respectively in monopolar and bipolar application of high-frequency electric current.

I claim:

1. High-frequency electrical surgical apparatus for use with manipulable electrodes through electrode-connections, respectively, for a neutral electrode, at least one electrode for monopolar operation, and at least two electrodes for bipolar operation, the apparatus having a high-frequency generator, an electric power source connected to the input circuit of said high-frequency generator for powering the same, and protective circuit means responsive to interruption of the electrically conducting connection between the neutral electrode and said electrode-connection at the apparatus provided for said neutral electrode, for interrupting the energy supply provided by said high-frequency generator to said at least one monopolar operation electrode and for producing an alarm signal indicative of said first-mentioned interruption, having the improvement which consists in that:

the output of said high-frequency generator is connected to the primary winding of a transformer having first and second secondary windings which are electrically isolated from each other and are of different turns ratios with respect to said primary winding, said first secondary winding having the turns ratio for coupling said high-frequency generator to the higher load impedance;

multipole switch-over means are provided having a first position in which said first secondary winding is connected to said electrode-connection for said at least one electrode for monopolar operation and to said electrode-connection for said neutral electrode while said electrode-connections for said electrodes for bipolar operation are disconnected from said transformer, and a second position in which said second secondary winding is connected to said electrode-connections for said electrodes for bipolar operation, while said electrode-connections for said electrode for monopolar operation and for said neutral electrode are disconnected from said transformer, said electrode connections for said electrodes for bipolar operation being electrically isolated from any conductor connectable by said switch-over means to said first secondary winding; and said multipole switch-over means includes means for disabling said protective circuit means when said multipole switch-over means is in its said second position.

2. High-frequency surgical apparatus as defined in claim 1 in which there are two of said electrode connections for said neutral electrode, both of which connect said neutral electrode to the same side of said first secondary winding in said first position of said switch-over means and in which apparatus said disabling means include connections for short-circuiting a portion of said protective circuit means which portion passes from one of said electrode-connections for said neutral electrode, through a part of said neutral electrode, and to the other of said electrode-connections for said neutral electrode.

3. High-frequency surgical apparatus as defined in claim 1 in which said first and second secondary windings are electrically dimensioned for coupling said high-frequency generator, respectively, to loads in the ranges of 600 to 300 ohms and 200 to 50 ohms.

4. High-frequency surgical apparatus as defined in claim 3 in which said first and second secondary windings are electrically dimensioned for coupling said high-frequency generator, respectively, to loads of about 500 ohms and about 100 ohms.

* * * * *